United States Patent [19]

Knöfel et al.

[11] 4,061,678
[45] Dec. 6, 1977

[54] PROCESS FOR THE PREPARATION OF AROMATIC POLYAMINES

[75] Inventors: Hartmut Knöfel, Leverkusen; Günther Ellendt, Krefeld, both of Germany

[73] Assignee: Bayer Aktiengesellschaft, Leverkusen, Germany

[21] Appl. No.: 645,042

[22] Filed: Dec. 29, 1975

[30] Foreign Application Priority Data

Jan. 9, 1975 Germany .............................. 2500573

[51] Int. Cl.$^2$ ............................................. C07C 85/24
[52] U.S. Cl. ......................... 260/570 D; 260/570.5 P; 260/570.9; 560/19
[58] Field of Search ....................... 260/570 D, 471 A

[56] References Cited

U.S. PATENT DOCUMENTS

| | | |
|---|---|---|
| 3,277,173 | 10/1966 | Powers et al. ...................... 260/570 |
| 3,478,099 | 11/1969 | Ross et al. ........................... 260/570 |
| 3,676,497 | 7/1972 | Recchia et al. ..................... 260/570 |

*Primary Examiner*—Robert V. Hines
*Attorney, Agent, or Firm*—Gene Harsh; Joseph C. Gil

[57] ABSTRACT

The instant invention is directed to a novel process for the production of aromatic polyamines. The process of the invention comprises a. condensing an aromatic amine with formaldehyde in the presence of a hydrophobic solvent and in the absence of an acid catalyst to produce a pre-condensate mixture containing the corresponding N,N'-disubstituted aminals, b. removing substantially all the water from said pre-condensate mixture to produce a first organic phase, c. extracting said first organic phase with an aqueous solution containing an acid catalyst thereby producing a second organic phase and an aqueous pre-condensate phase which contains said aminals, d. subjecting said aqueous pre-condensate phase to a rearrangement reaction thereby producing an aqueous condensation mixture containing said aromatic polyamines, e. extracting said aqueous condensation mixture with a hydrophobic solvent to provide a solvent phase and an aqueous phase which comprises an aqueous solution containing the acid catalyst as an amine salt of said aromatic amine, and said aromatic polyamines, f. recovering aromatic polyamines from said solvent phase, and g. returning said aqueous phase to step (c).

In the presently preferred embodiment, the organic phase of step (c) is returned to step (a).

6 Claims, 1 Drawing Figure

PROCESS FOR THE PREPARATION OF AROMATIC POLYAMINES

BACKGROUND OF THE INVENTION

In U.S. application Ser. No. 383,921, filed July 30, 1973 and now U.S. Pat. No. 3,996,283, there is described a process for the preparation of multinuclear aromatic polyamines by the condensation of aromatic amines with formaldehyde in the presence of water and acid catalysts In that process, the aqueous condensation mixture obtained after the reaction has been completed is extracted with a hydrophobic solvent. The resulting solvent phase is then worked-up to recover the desired polyamine, while the aqueous phase, which contains the acid catalyst in the form of amine salts, is returned to the beginning of the process with the addition of fresh amine as starting material.

The above-mentioned process marked a major improvement over the previously known process of aniline/formaldehyde condensation carried out with acid catalysts, particularly since it obviated the need for neutralization of the acid catalyst. As a result of this, the effluent water from the process is substantially free from salt and the corresponding consumption of acid catalyst and alkalizing agent is virtually zero. This process, however, has some disadvantages. Thus, the circulation of the aqueous catalyst includes varying quantities of water added from outside (depending on the quantity of formaldehyde which is introduced in the form of aqueous solutions and depending on the quantity of the water produced in the condensation reaction) and this additional water must be removed from circulation, generally by distillation.

It is therefore, an object of the present invention to improve the above process with a view towards keeping the quantity of water in the circulation of aqueous catalyst constant. In other words, the purpose of the instant invention is to relieve the circulation of additional water introduced from outside or formed chemically and at the same time to enable the water introduced and formed in the reaction to be removed by a simple water separator. From a processing point of view, the quantitative removal of the varying quantities of water added in the course of the reaction from the aqueous catalyst would significantly increase the flexibility of the system since the catalyst circulation could be kept constant even with varying outputs and with varying aniline/formaldehyde ratios and hence with varying quantities of water introduced into the process. It would therefore be possible to produce various types of polyamine always under optimum conditions. The elimination of the distillation step to remove the water introduced and formed in the course of the reaction would further simplify and improve the prior process.

DESCRIPTION OF THE INVENTION

Figure 1:
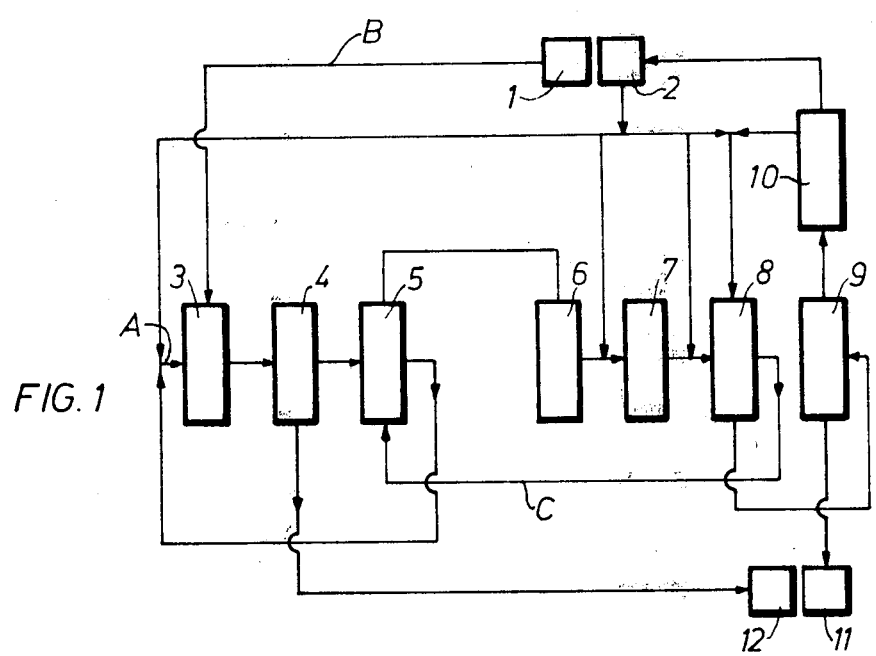
FIG. 1 represents a flow diagram illustrating one embodiment of the present invention.

The present invention therefor relates to a process for the preparation of multi-nuclear aromatic polyamines by condensation of aromatic amines with formaldehyde in the absence of acid catalysts to produce the corresponding N,N'-disubstituted aminals, followed by molecular rearrangement of these aminals to multi-nuclear aromatic polyamines in the presence of water and acid catalysts, followed by extraction of the resulting aqueous reaction mixture with a hydrophobic solvent (which in the preferred embodiment is down by the addition of the same aromatic amine as that used for condensation), working-up of the resulting solvent phase in known manner to obtain the multi-nuclear aromatic polyamine and return of the aqueous phase which contains the acid catalyst, characterized in that:

a. condensation of the aromatic amine with formaldehyde is carried out in the presence of a hydrophobic solvent;

b. the water of condensation and any water introduced with formaldehyde are removed from the system by means of a water separator;

c. the organic phase leaving the water separator, which contains aminal, is extracted with the aqueous phase which has been returned from the end product extraction and which contains acid catalyst; and in the most preferable embodiment, d. the organic phase leaving the extraction stage described under (c) is returned to the beginning of the operating cycle.

More particularly, the instant invention is directed to a process for the preparation of a multi-nuclear aromatic polyamine comprising a. condensing an aromatic amine with formaldehyde in the presence of a hydrophobic solvent and in the absence of an acid catalyst to produce a pre-condensate mixture containing the corresponding N,N'-disubstituted aminals, b. removing substantially all the water from said pre-condensate mixture to produce a first organic phase, c. extracting said first organic phase with an aqueous solution containing an acid catalyst thereby producing a second organic phase and an aqueous pre-condensate phase which contains said aminals, d. subjecting said aqueous pre-condensate phase to a rearrangement reaction thereby producing an aqueous condensation mixture containing said aromatic polyamines, e. extracting said aqueous condensation mixture with a hydrophobic solvent to provide a solvent phase and an aqueous phase which comprises an aqueous solution containing the acid catalyst as an amine salt of said aromatic amine, and of said aromatic polyamines, f. recovering aromatic polyamines from said solvent phase, and g. returning said aqueous phase to step (c). In the preferred embodiment, the organic phase produced in step (c) is returned to step (a).

The principle of the process according to the invention will first be described and reference to the drawing. In this drawing, 1. represents a tank for an aqueous formaldehyde solution;
2. a tank for aniline;
3. a condensation reactor;
4. a water separator;
5. an extractor;
6. a molecular rearrangement reactor;
7. a second rearrangement reactor;
8. an extractor;
9. a distillation column;
10. a second distillation column;
11. a tank for the product of the process, and
12. a tank for effluent water.

Catalyst-free reaction of aniline with formaldehyde to the corresponding N,N'-diphenylaminal or more highly condensed N-substituted homologues takes place in 3. This reaction is carried out in the presence of hydrophobic solvents which are circulated through 3, 4 and 5. The water introduced with the formaldehyde or formed in the condensation reaction is removed from the two phase system in the water separator 4 by simple phase separation based on density differences. The solvent phase leaving the water separator enters the extractor 5, which is preferably a multi-stage extractor, where the aminal formed in the reaction is washed out of the solvent phase by a single stage or, preferably, multi-stage extraction process by means of the aqueous phase leaving the extractor 8, the aminal being optionally exchanged by aniline from the aqueous phase. The solvent phase leaving the extractor 5, which may carry free aniline introduced during the extraction process, is then preferably returned to the condensation reactor 3.

The pre-condensate now combined with the aqueous catalyst flows from extractor 5 into the reactor 6 where it mainly undergoes the first rearrangement to the singly N-substituted intermediate product. Rearrangement to the final product of the process thereafter takes place in reactor 7, if desired, after further addition of aniline.

The aqueous phase containing the product of the process is then transferred from reactor 7 to the extractor 8, if desired, after further addition of aniline. In the extractor 8, the product of the process is removed from the aqueous phase by extraction with a hydrophobic solvent. The solvent phase leaving the extractor 8 is worked-up by distillation in the distillation columns 9 and 10. The solvent leaving the distillation column 10 is returned to the extractor 8. If desired, further aniline is added to the solvent. The product of the process is obtained as sump product of column 9. The aqueous phase leaving extractor 8, which contains the catalyst, is then returned to the extractor 5.

The above description serves to explain the basic principle of the invention. Instead of utilizing aniline, the process according to the invention may, of course, be carried out with other aromatic amines, examples of which are mentioned below. Moreover, the molecular rearrangement reaction may, of course, be carried out in one reactor or in more than two reactors. Similarly, several extraction stages may be employed for extracting the product of the process. Isolation of the organic phase by distillation could also be carried out in one distillation column or in more than two. The only essential features of the invention are the steps (a) through (g) described above.

Any aromatic amines may be used in the process according to the invention. Such amines include aniline, o-toluidine, m-toluidine, N-methylaniline, N-ethylaniline, 2,6-dimethylaniline, 2,6-diethylaniline, 2,6-diisopropylaniline, 2,4-diaminotoluene, anthranilic acid alkyl esters which contain from 1 to 4 carbon atoms in the alkyl group, and mixtures thereof. The aromatic amine preferably used in the process according to the invention is aniline.

The acids used in the process according to the invention are preferably water-soluble acids with a pKA below 2.5 and preferably below 1.5. Examples include hydrochloric acid, hydrobromic acid, sulphuric acid, trifluoroacetic acid, methanesulphonic acid, trifluoromethanesulphonic acid, benzenesulphonic acid or phosphoric acid. The presently preferred catalyst is hydrochloric acid. The above-mentioned acids may also be used as mixtures with acid salts or neutral salts of such acids, for example the corresponding ammonium or alkali metal salts. In the process of the instant invention, the abovementioned acids are present in the aqueous system in the form of amine salts of the aromatic amines in the aqueous cycle. For the start of the cyclic process the acids are preferably added as aqueous aniline salt solution into extractor 5.

Hydrophobic solvents which are suitable for use in the process of the instant invention include any solvents with a boiling point in the range of from about 30° to 250° C, preferably from 80° to 200° C, which are immiscible with water and inert towards the reaction components. The following are examples of particularly suitable solvents: chlorobenzene, dichlorobenzenes, benzene, toluene, xylenes, dichloroethane, chloroform, carbon tetrachloride and the like. The presently preferred solvent is o-xylene. The amine used as a starting reactant of the process or some other aromatic amine may, if desired, serve as the hydrophobic solvent in which case, it would be added at that stage of the process where necessary. In the extraction step (e) the solvents are generally used in a volumetric ratio of acid condensation mixture to solvent of from 5:1 to 1:10 and preferably from 2:1 to 1:5.

Formaldehyde, which is the other starting material used with the aromatic amine in the process according to the invention, is preferably introduced into the process in the form of an aqueous formalin solution.

At the beginning of the condensation reaction (reactor 3), the molar ratio of aniline to formaldehyde is generally from 1:1 to 20:1 and preferably from 2:1 to 5:1.

The volumetric ratio of (aniline + formaldehyde) to (water) at the beginning of the condensation reaction is generally from 1:1 to 12:1, although this ratio is not essential to the process of the instant invention.

The volumetric ratio of (aqueous amine salt solution) to (solvent phase) in extractor 5 is generally from 5:1 to 1:5 and preferably from 3:1 to 1:3.

The solvent phase leaving the extractor 5 may contain up to 80% by weight and preferably contains up to 60% by weight, of free aniline. In addition, it may contain portions of precondensate and/or products of the process. The aniline content in this solvent phase and the presence of precondensates and products of the process in the solvent phase are primarily due to an exchange of these amines for products of the individual stages of the process in extractor 5. Any precondensates present in the solvent phase leaving the extractor 5, in particular N,N'-disubstituted aminal, may be attributed to the fact that extraction in extractor 5 does not proceed quantitatively, but this does not impair the progress or outcome of the process.

In addition to precondensates, the aqueous phase introduced into reactor 6 contains primarily the major portion of the product of the process and free aniline which was already present in the aqueous phase leaving the extractor 8. Since extraction of the products of the process in the main extractor 8 does not proceed quantitatively and both phases leaving the extractor 8 always contain an equilibrium mixture of starting amine and products of the process, some of the products of the process also return to the extractor 5. This also does not impair the progress or outcome of the process. The above-mentioned amines are partially protonized by the acid catalyst. The degree of protonation (degree of protonation = percentage of total quantity of amine nitrogen atoms present as amine salt groups) is always below 100% at the input to reactor 6 even if the degree of protonation is 100% in the aqueous phase returned from the extractor 8. It is, in fact, one of the advantages of the process according to the invention that the degree of protonation may be varied within wide limits before the entry into the first rearrangement stage 6 while the aqueous catalyst circulation is kept constant.

The degree of protonation and the entry into the first rearrangement stage is generally from 10 to 95% and preferably from 30 to 90%. The degree of protonation may be varied (a) by increasing the quantities of free amine remaining in the aqueous phase if the efficiency of the extractors decreases; and (b) by variation of the rate of flow of substance into the extractors and necessarily the amine content of the solvents carried through the extractors.

The molecular arrangement is preferably carried out in two stages (reactors 6 and 7) in the process according to the invention. Rearrangement of the primary precondensates such as N,N'-disubstituted aminal to singly N-substituted intermediate products generally takes place in the first reactor 6, and rearrangement of the said intermediate products to the desired end products takes place in the second reactor 7. Where two reactors are used, it may be advisable to reduce the degree of protonation of the aqueous reaction mixture leaving the reactor 6 by further addition of aniline.

The aqueous reaction mixture is then transferred from the last rearrangement stage 7 to extraction in the extractor 8. The hydrophobic solvent used in this extractor preferably has a free aniline content of from 0 to 80% by weight and preferably from 20 to 60% by weight. At the entry into the extractor 8, the aqueous phase generally contains from 10 to 60% by weight and preferably from 12 to 30% by weight, of free i.e., non-protonized amine. This free amine content can be adjusted by the addition of aniline after the last rearrangement stage 7 if sufficient aniline has not already been added to the aqueous phase before its entry into the last rearrangement stage 7.

The concentration of free amines in the aqueous phase and in the organic phase is preferably adjusted so that the solution pressure of free aromatic amine in the aqueous phase at its entry into the extractor 8 is equal to the solution pressure of aromatic amine in the organic phase at the same point of the extraction stage.

The organic phase leaving the extractor 8 is separated into the desired aniline/formaldehyde condensate on the one hand and solvent and aniline on the other by distillation in known manner. Separation of the last two components mentioned may be omitted if solvent which contains aniline is used in extractor 8 (or in all stages in the case of multistage extraction). The aqueous solution leaving the extraction stage is returned to the extractor 5 (the degree of protonation of the aqueous solution leaving the extractor 8 is generally from 30 to 70%). If desired, free amine may be removed from the aqueous solution by an additional extraction, preferably with solvent which is free from amine (not shown in the drawing and not essential to the invention) before the solution is returned to the extractor 5 so that the aqueous phase returning to extractor 5 has a degree of protonation of close to 100%.

The following temperatures are preferably employed in the process according to the invention:

Precondensation (reactor 3) at from 0° to 80° C, in particular from 20° to 60° C;

Water separation in separator 4 at from 5° to 80° C, in particular from 20° to 60° C;

Extraction in extractor 5 at from 20° to 110° C, in particular from 20° to 60° C;

Rearrangement reaction, if carried out in several stages, at from 20° to 40° C in the first rearrangement reactor 6 and at from 60° to 110° C in the last rearrangement reactor 7;

Main extraction 8 generally at from 70° to 110° C preferably at from 80° to 100° C.

The nature of the apparatus used in the process according to the invention is not an essential part of the invention. Thus, for example, the process may be carried out using tube reactors or liquid-liquid extractors and phase separators commonly used in industrial chemistry.

The process according to the invention may, of course, be carried out in apparatus different from that exemplified in the drawing. All stages of the process (precondensation, water separation, first extraction, rearrangement reaction and second extraction) may, if desired, be carried out as single stage or multi-stage operations. In one embodiment of the process according to the invention, the two phases are kept for an increased length of time in the extraction stage 5 and/or a higher temperature is employed in extraction step 5 so that a considerable proportion of the aminals are already rearranged to intermediate products which are monosubstituted in the nucleus and even to end products in extraction stage 5. Such a procedure in many cases obviates the need for a multi-stage rearrangement. In particular, in this embodiment of the process, temperatures above 40° C (from 40° to 110° C) are preferably employed in the extractor 5. The aromatic amine used as starting material may, as indicated above, be fed into the system at any point in the process according to the invention (at inlet pre-condensation and/or inlet to last rearrangement stage and/or inlet to extraction stage 8). In the extreme case, the total quantity of starting aromatic amine could even be added to the solvent used for extraction in stage 8. In that case, free starting amine would also enter the aqueous phase since the amine salts dissolved in the aqueous phase function as solution aids for free amine in water, and finally the free starting amines would enter the first reactor 3 by way of extractor 5.

EXAMPLE 1

In describing this example, reference will be made to FIG. 1.

A 40% solution of an aromatic amine mixture in o-xylene (A) and 30% aqueous formaldehyde solution (B) from container 1 are continuously introduced into a continuously operating experimental laboratory plant consisting of two stirrer vessels arranged behind one another. The two streams of substance have the following composition in grams per hour:

Stream (A)
  2400 o-xylene
  1600 aniline and aniline-formaldehyde condensates
Stream (B)
  108 formaldehyde and 252 water.

The temperature in the two vessels of reactor 3 is maintained at 35° C with vigorous stirring and cooling, and the substances then enter the separator 4 which is also maintained at 35° C and in which about 317 g/hour of water is removed from the aqueous phase of the diphasic system, which is kept at a constant level.

The organic phase from separator 4 is transferred to an extraction column which functions as a two- or three- stage extractor and in which it is continuously extracted at 35° C with the aqueous stream (C) which has the following composition (gram/hour):

Stream (C)
 1340 aniline
 123 polyarylamines
 547 hydrogen chloride
 2460 water.

The aqueous phase from 5 flows through a cascade of 6 stirrer vessels (reactors 6 and 7) in which the temperature rises from 35° C to 95° C.

The organic phase from 5 is adjusted to its original aromatic amine content by the addition of aniline and again reacted with formaldehyde as stream A. Before the addition of aniline it is advisable to extract the water removed from 4 with the xylene phase separated in 5.

The aqueous phase leaving extraction column 5 is adjusted to an amine content of about 50% by weight, by the addition of aniline and then enters the extraction system 8 which consists of a first extraction column followed by a second extraction column. In the first extraction column the reaction product is extracted at a temperature of from 90° to 95° C from the aqueous reaction mixture to which aniline has been added, using as extraction medium the organic phase from the second extraction column, to which 4825 g/h of aniline have been added. The substance used for extraction in the second extraction column is 5830 g/h of o-xylene.

The organic phase leaving the extraction system 8 is separated into aniline, o-xylene and polyarylamine (approximately 700 g/h) in the distillation apparatus 9 and 10. The recovered aniline together with fresh aniline added to the system is passed through container 2 to be distributed to the various feed points in the reaction cycle.

The product obtained when the process according to the invention is carried out as described above has the following average composition in the dinuclear portion:

2,2'-diaminodiphenylmethane: 0.1% by weight
2,4'-diaminodiphenylmethane: 6.7% by weight
4,4'-diaminodiphenylmethane: 93.2% by weight.

What is claimed is:
1. A process for the preparation of multi-nuclear aromatic polyamines comprising:
 a. condensing an aromatic amine with formaldehyde in the presence of a hydrophobic solvent and in the absence of an acid catalyst to produce a pre-condensate mixture containing the corresponding N,N'-disubstituted aminals,
 b. removing substantially all the water from said pre-condensate mixture to produce a first organic phase,
 c. extracting said first organic phase with an aqueous solution containing an acid catalyst thereby producing a second organic phase and an aqueous pre-condensate phase which contains said aminals,
 d. subjecting said aqueous pre-condensate phase to a rearrangement reaction thereby producing an aqueous condensation mixture containing said aromatic polyamines:
 e. extracting said aqueous condensation mixture with a hydrophobic solvent to provide a solvent phase and an aqueous phase which comprises an aqueous solution containing the acid catalyst as an amine salt of said aromatic amine, and of said aromatic polyamines,
 f. recovering aromatic polyamines from said solvent phase, and
 g. returning said aqueous phase to step (c).

2. The process of claim 1, further comprising (h) returning the said second organic phase to step (a).

3. The process of claim 2, wherein said aromatic amine is aniline.

4. The process of claim 3, wherein said acid catalyst is hydrochloric acid in the form of hydrochlorides of aniline and aniline/formaldehyde condensates.

5. The process of claim 4, wherein said hydrophobic solvents are both xylene.

6. The process of claim 1 wherein a mixture of said aromatic amine and a hydrophobic solvent is used in step (e).

* * * * *